United States Patent [19]

Armstrong

[11] 3,933,871

[45] Jan. 20, 1976

[54] FABRIC SOFTENER COMPOUND AND PROCESSES FOR PREPARING AND USING THE SAME

[75] Inventor: Leonard J. Armstrong, Janesville, Wis.

[73] Assignee: Armstrong Chemical Company, Inc., Janesville, Wis.

[22] Filed: Nov. 12, 1973

[21] Appl. No.: 415,143

[52] U.S. Cl. ................. 260/401; 260/404.5; 8/137; 252/8.75

[51] Int. Cl.² ........................................ C07C 103/38

[58] Field of Search ...................................... 260/401

[56] References Cited

UNITED STATES PATENTS

| | | | |
|---|---|---|---|
| 2,583,772 | 1/1952 | Gunderson | 260/401 |
| 3,492,324 | 1/1970 | Blackman | 260/401 X |
| 3,703,535 | 11/1972 | Mannheimer | 260/401 |

*Primary Examiner*—Patrick P. Garvin
*Attorney, Agent, or Firm*—Carl C. Batz

[57] ABSTRACT

A fabric softener compound having the formula:

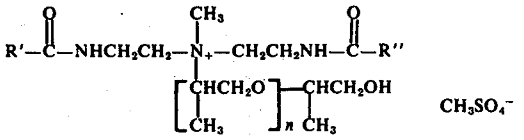

wherein R′ and R″ are alkyl or alkylene radicals having from 10 to 20 carbons in their carbon chains and $n$ = 0 to 4.

Also methods for preparing such compounds in which propylene oxide is reacted with an intermediate compound having the formula:

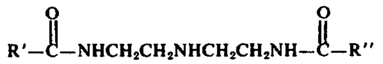

wherein R′ and R″ are alkyl or alkylene radicals having from 10 to 20 carbons in their carbon chains.

Also processes for washing fabrics utilizing said fabric softening compound.

5 Claims, No Drawings

FABRIC SOFTENER COMPOUND AND PROCESSES FOR PREPARING AND USING THE SAME

This invention relates to a fabric softening compound, and particularly to a propoxylated fabric softening compound having the following formula:

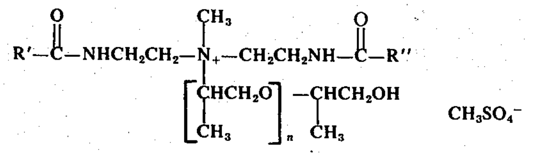

wherein R' and R'' are long chain alkyl or alkylene groups and $n = 0$ to 4.

BACKGROUND

Ethoxylated diamidoamine quaternary of dimethyl sulfate is a well known compound used for the softening of fabric. It is made by reacting a long chain glyceride such as tallow with diethylene triamine at elevated temperatures to produce a diamidoamine represented by the following structure:

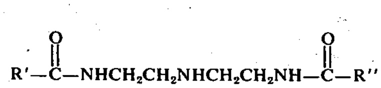

wherein R' and R'' are long chain alkyl or alkylene groups.

This diamidoamine is then treated with ethylene oxide to give a tertiary amine having the following structure:

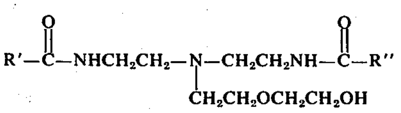

wherein R' and R'' are long chain alkyl or alkylene groups.

This tertiary amine is then reacted with dimethyl sulfate to prepare the compound represented by the following formula:

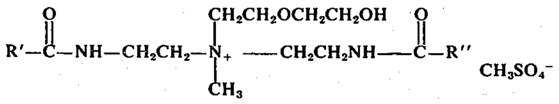

wherein R' and R'' are long chain alkyl or alkylene groups. This compound is now being used commercially for fabric softening.

This compound has good hydrophilic balance and other characteristics desired in a fabric softening compound. However, it has a serious disadvantage in that under common conditions of use heating is required to maintain the compound fluid and it would be very desirable to have a softening compound like this one which retains all of the desirable attributes of this known compound, but which will remain flowable at lower temperatures.

I have discovered that treating the diamidoamine with propylene oxide instead of ethylene oxide as above referred to I can obtain a compound having the favorable characteristics known to the ethoxylated compound of the art and having in addition the quality of being fluid at substantially lower temperatures.

This discovery is unexpected because it is known that propylene oxide when reacted with amines, acids or alcohols tends to increase the hydrophobic character and oil solubility of the resulting molecule. Further, the longer carbon chain of the propoxy group might be expected to decrease the fluidity of the resulting compound.

In the preparation of the improved diamidoamine quaternary compounds, I may start with the reaction of tallow and diethylene triamine. Or, in the palce of tallow I may use any available source of material which in the reaction will yield alkyl or alkylene radicals having from 10 to 20 carbons in the hydrocarbon chain such as lauric, myristic, palmitic, oleic, linoleic or stearic acids. Conveniently, I can use the common oils such as tallow, lard or other animal or vegetable oils such as corn oil, coconut oil, tall oil or soya oil, or the fatty acid mixtures therefrom, or the fatty acid esters thereof. My improved compounds made from vegetable oils or acids therefrom are useful outside the area of household fabric softeners in fields such as textile treatment or cationic chemistry applications.

The tallow or other fatty oils, or acids or esters above referred to, is reacted with diethylene triamine which is commercially available and in its commercial form may contain small quantities of ethylene diamine and triethylene tetramine.

The reaction may be conducted using about one mole of diethylene triamine to from 0.6 to 0.7 (0.66 preferred) moles of tallow with stirring and using temperatures of about 250° to 300°F. for several hours, after which the resulting reaction product is cooled suitable to below 200°F..

This intermediate product is then reacted with propylene oxide at a temperature of about 180° to 250°F., preferably about 190° to 210°F., with stirring, using propylene oxide in the mole range of 1.0 to 5.0 to 1 mole of the intermediate reaction product to obtain a propoxylated material having the following formula:

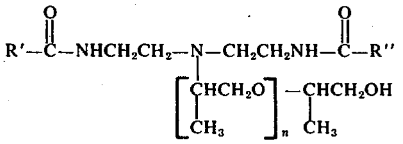

where $n = 0$ to 4.

To a quantity of this propoxylated material may be added a solvent such as isopropanol, ethanol, methanol, diethylene glycol, hexylene glycol, or the like, in a proportion of about 1 part solvent to 10 to 11 parts by weight of the propoxylated material, and dimethyl sulfate in a proportion of about 1 part dimethyl sulfate to about 6 to 10 weight parts of the propoxylated solution in a range of 0.90 to 1.0 moles (preferably 0.95) to 1 mole of the propoxylated reactant material. Good agitation should be provided. Then a further quantity of solvent may be added to give a finished compound of about 90% solids. The resulting product contains the reaction product represented by the following formula:

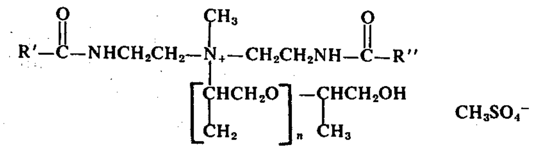

where $n = 0$ to 4.

In the reaction between the diamido amine and the propylene oxide one mole of propylene oxide is entered into the reaction, and if further quantities of propylene oxide are available another mole may be entered, and then another, etc., up to about 5 moles in the resulting product.

Where it is desired to obtain a final product having a formula in which $n = 0$, it may suffice to use propylene oxide in a molar ratio of one mole of propylene oxide to one mole of the intermediate reaction product, but to obtain a reaction product having a formula where $n$ is 1, I may use a molar ratio of propylene oxide to the amine intermediate product of about 2:1. In each case, this ratio will be $n = 1$ moles of propylene oxide to one mole of the amine.

It is further understood that in most cases, the reaction product may contain mixtures of compounds in which one or more, up to 5 moles of propylene oxide, are added in the reaction, and in which n, in the formula above given, varies from 0 to 4. The addition reaction becomes more difficult as the number of moles of propylene oxide increases. In order to speed this reaction and to facilitate the addition of the larger numbers of moles of propylene oxide it has been found helpful to add small quantities of a caustic catalyst. For example, I may add sodium hydroxide in a proportion of about 0.0005 to 0.002 parts by weight of sodium hydroxide to one part of the reaction mixture.

As above explained, the reaction product may contain a mixture of compounds in which n of the above formula may vary from 0 to 4. I have found that very desirable products may be obtained where the mixture has a predominance of compounds where $n$ is 0, or wherein $n$ is 1. The formula where $n = 0$ becomes:

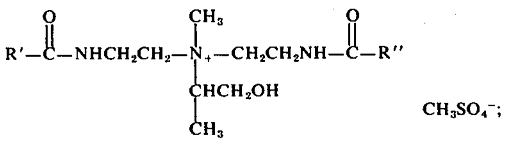

and where $n$ is 1, becomes:

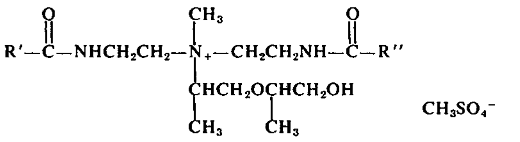

Examples illustrating the preparation of my improved compounds and for testing their characteristics are given as follows:

EXAMPLE I

Preparation of Propoxylated Diamidoamine Quaternary Compounds

To an autoclave equipped with mechanical stirrer was charged 800 g. (0.91) mole) bleached tallow and 143.5 g. (1.4 mole) diethylene triamine. The stirred mixture was heated under a nitrogen atmosphere at 260° to 280°F. for 4 hours.

The diamidoamine intermediate was then cooled to 200°F. and 230 g. (3.96 mole) propylene oxide was added at 190° to 210°F.. After propylene oxide addition, the propylated material had a color of only Gardner Hellige 2+.

To 1067 g. of the propoxylated material was added 100 g. of isopropanol, and at 130° to 150°F. 155g. (1.23 moles) of dimethyl sulfate was added with good agitation. An additional 35 g. of isopropanol was added to give a finished quaternary compound of 90% solids. This product had a Gardner Hellige color of 3.

EXAMPLE II

Preparation of Propoxylated Diamidoamine Quaternary Compounds

To an autoclave equipped with mechanical stirrer was charged 880 g. (1 mole) bleached refined lard and 154.5 g. (1.5 moles) diethylene triamine. The stirred mixture was heated under a nitrogen atmosphere of 260° to 280°F. for 4 hours.

The diamidoamine intermediate was then cooled to 200°F. and 151 g. (2.6 moles) propylene oxide was added at 190° to 210°F. After propylene oxide addition, the propylated material had a color of only Gardner Hellige 2+.

To 1120 g. of propoxylated material was added 130 g. isopropanol, and at 130° to 150°F. 174 g. (1.38 moles) of dimethyl sulfate was added with good agitation. An additional amount of isopropanol was added to give a finished quaternary compound of 90% solids.

EXAMPLE III

Preparation of Propoxylated Diamidoamine Quaternary Compounds

To an autoclave equipped with mechanical stirrer was charged 777 g. (1.17 moles) refined coconut oil and 180 g. (1.75 moles) diethylene triamine. The stirred mixture was heated under a nitrogen atmosphere at 260° to 280°F. for 4 hours.

The diamidoamine intermeditate was then cooled to 200°F. and 244 g. (4.2 moles) propylene oxide was added at 190° to 210°F.. After propylene oxide addition, mixture was cooked an additional 2 hours at 190° to 210°F..

To 1142 g. of the propoxylated material was added 140 g. of isopropanol, and at 130° to 150°F. 200 g. (1.59 moles) of dimethyl sulfate was added with good agitation. An additional amount of isopropanol was added to give a finished quaternary compound of 90% solids.

EXAMPLE IV

Preparation of Propoxylated Diamidoamine Quaternary Compounds

In a small pilot plant run, 1840 No. of bleached tallow and 325 No. of diethylene triamine were charged to a reactor and heated at 260° to 280°F. for 4 hours.

Product was then cooled to 200°F. and 250 No. of isopropanol was added, followed by addition of 300 No. of propylene oxide at 180° to 220°F., using approximately 1.6 moles of propylene oxide to 1 mole of amido amine.

After propylene oxide addition was completed, the reaction mixture was cooled to 120° to 140°F. and 400 No. of dimethyl sulfate was added within the 120° to 140°F. range. This product was a yellow liquid with a Gardner Hellige color of 5 + a solid content of 90.5 and a pH at 10% in IPA water solution of 5.0.

EXAMPLE V

Fluidity Characteristics

The compound prepared in accordance with Example I was tested for fluidity and found when at 90% activity to be a flowable liquid at 80°F..

A compound was prepared in exactly the same way as in Example I except that ethylene oxide was used instead of propylene oxide. The resulting compound was tested and found not to be flowable at 80°F..

EXAMPLE VI

Softening Properties

Softening dispersions were prepared at 3.2% solids using (a) the compound as prepared as in Example I, and (b) the compound prepared as stated in Example V, second paragraph.

Using a 6 pound wash load consisting of towels, the dispersion sample using compound (b) was added at the rinse cycle. In a similar load the dispersion sample using compound (a) was added at the rinse cycle.

The towels were line dried. Test panel attempts to differentiate softening properties of the towels failed to show any difference between the towels washed by these two loads. All the towels were well softened.

EXAMPLE VII

Stability of Dispersion

Samples of 3% solids dispersion of the compounds prepared as in Example I were prepared in water of 150 ppm hardness and stored at room temperature, at 40° and at 105°F.. The dispersions were all still stable at the end of three months.

EXAMPLE VIII

High Solids Dispersion Fluidity

Both 16% and 20% solids dispersions were prepared, based on the weight of the compound prepared as in Example I and also based on the compound as set forth in the second paragraph of Example V.

The following procedure was used for producing the dispersions. Water of 150 ppm hardness was heated to 120°F. To the water was added 0.2% sodium chloride by weight of the total dispersion. The softener base or quaternary was then added slowly to the rapidly stirred water. As the dispersion viscosity appeared to increase further increments of sodium chloride were added until 0.8% by weight of the total dispersion was added. After the remainder of the softener base was added, a final 0.2% salt was added to give a total of 1.0% sodium chloride in the finished dispersion.

Dispersions were chilled overnight at 40°F. and viscosities measured using a No. 2 Spindle at 30 rpm. Dispersion viscosities were given in the following table:

| Weight % of Quaternary Compound | Propoxylated Quaternary Compound Viscosity at 76 F. cps | Ethoxylated Quaternary Compound Viscosity at 76 F. cps |
|---|---|---|
| 16 | 400 | 600 |
| 20 | 670 | >2000 |

The above examples are intended to be illustrative only and not as limiting the invention. It will be apparent from the Examples that considerable variation is possible in the method of manufacturing typical compounds within the group which they represent. It is also apparent that numerous other modifications may be devised by those skilled in the art without departing from the spirit and scope of the invention.

I claim:

1. A compound having the following formula:

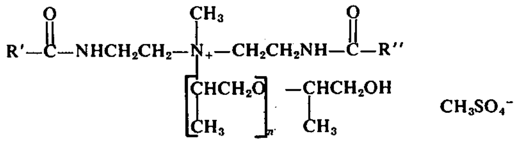

wherein R' and R'' are alkyl or alkylene radicals having from 10 to 20 carbons in their carbon chains and $n$ + 0 to 4.

2. A compound as set forth in claim 1 wherein R' and R'' are alkyl or alkylene radicals of tallow.

3. A compound as set forth in claim 1 wherein R' and R'' are alkyl or alkylene radicals of lard.

4. A compound having the following formula:

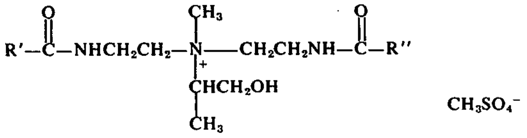

wherein R' and R'' are alkyl or alkylene radicals having from 10 to 20 carbons in their carbon chain.

5. A compound having the following formula:

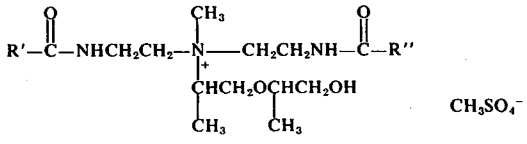

wherein R' and R'' are alkyl or alkylene radicals having from 10 to 20 carbons in their carbon chain.

* * * * *

UNITED STATES PATENT OFFICE

CERTIFICATE OF CORRECTION

Patent No. 3,933,871 Dated January 20, 1976

Inventor(s) Leonard J. Armstrong

It is certified that error appears in the above-identified patent and that said Letters Patent are hereby corrected as shown below:

Column 2, line 10, "palce" should read --- place ---.
Column 6, lines 32 and 33, "n + 0 to 4" should read --- n = 0 to 4 ---.

Signed and Sealed this

First Day of February 1977

[SEAL]

Attest:

RUTH C. MASON
*Attesting Officer*

C. MARSHALL DANN
*Commissioner of Patents and Trademarks*